United States Patent [19]

Hengartner et al.

[11] Patent Number: 5,120,759
[45] Date of Patent: Jun. 9, 1992

[54] TETRAHYDRONAPHTHALENE DERIVATIVES FOR IMPROVING SHORT-TERM MEMORY

[75] Inventors: Urs Hengartner, Basel; Henri Ramuz, Birsfelden, both of Switzerland

[73] Assignee: Hoffmann-La Roche Inc., Nutley, N.J.

[21] Appl. No.: 690,408

[22] Filed: Apr. 23, 1991

Related U.S. Application Data

[62] Division of Ser. No. 495,075, Mar. 15, 1990, abandoned.

Foreign Application Priority Data

Mar. 20, 1989 [CH] Switzerland ............ 1074/89

[51] Int. Cl.$^5$ ............ A61K 31/335; A61K 31/36; C07D 319/18; C07D 314/48
[52] U.S. Cl. ............ 514/452; 549/362; 549/435; 549/444; 549/462; 549/484; 549/486; 560/152; 560/187; 560/250; 560/25; 514/466; 514/469; 514/471; 514/550; 514/546
[58] Field of Search ............ 549/362, 435, 444, 484, 549/462, 486; 560/152, 187, 250, 252; 514/452, 466, 469, 471, 550, 546

[56] References Cited

U.S. PATENT DOCUMENTS 4,680,310  7/1987  Hengartner et al. ............ 514/539
4,808,605  2/1989  Branca et al. ............ 514/394

FOREIGN PATENT DOCUMENTS 177960  4/1983  European Pat. Off. .
080721  6/1983  European Pat. Off. .
268148  5/1988  European Pat. Off. .

OTHER PUBLICATIONS

Chemical Abstracts, 111:442f (1989).
J. Cardio. Pharm. 13(5) 754 (1989).

*Primary Examiner*—Nicky Chan
*Attorney, Agent, or Firm*—George M. Gould; William G. Isgro; William Krovatin

[57] ABSTRACT

Novel compounds of the formula

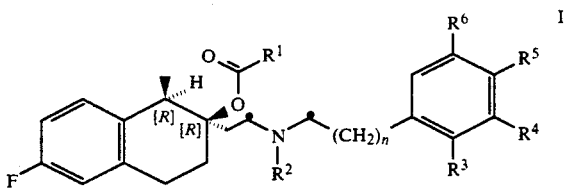

wherein $R^1$ is lower-alkyl, lower-alkoxy-lower-alkyl, lower-alkylthio-lower-alkyl or furyl, $R^2$ is lower-alkyl, phenyl-lower-alkyl or cyclohexyl-lower-alkyl, each of $R^3$ and $R^6$ independently is hydrogen or fluorine, each of $R^4$ and $R^5$ independently is hydrogen or lower-alkoxy or together are methylenedioxy, ethylenedioxy or ethylenoxy and n is an integer from 1 to 3, have a pronounced activity in counteracting cerebral insufficiency or improving cognitive functions and also reduce the multiple-resistance towards cytostatics in the treatment of tumors or of chloroquine resistance in the treatment of malaria. They can accordingly be used as medicaments, especially for the control or prevention of cerebral insufficiency or for the improvement of cognitive functions. The novel compounds of formula I can be manufactured by O-acylating a likewise novel compound of the formula

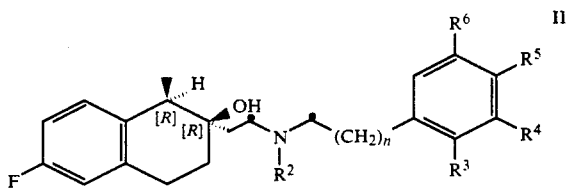

wherein $R^2$ is lower-alkyl, phenyl-lower-alkyl or cyclohexyl-lower-alkyl, each of $R^3$ and $R^6$ independently is hydrogen or fluorine, each of $R^4$ and $R^5$ independently is hydrogen or lower-alkoxy or together are methylenedioxy, ethylendioxy or ethylenoxy and n is an integer from 1 to 3.

18 Claims, No Drawings

TETRAHYDRONAPHTHALENE DERIVATIVES FOR IMPROVING SHORT-TERM MEMORY

This is a division of copending application Ser. No. 07/495,075 filed on Mar. 15, 1990, now abandoned.

BACKGROUND OF THE INVENTION

Field of the Invention

The present invention relates to tetrahydronaphthalene derivatives and to starting materials thereof.

SUMMARY OF THE INVENTION

The present invention relates to tetrahydronaphthalene derivatives, and in particular, is concerned with tetrahydronaphthalene derivatives having the formula

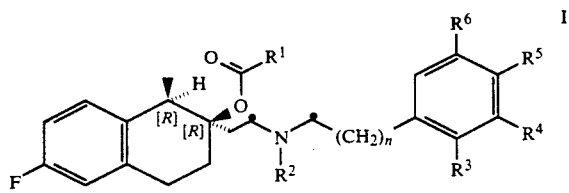

where $R^1$ is lower-alkyl, lower-alkoxy-lower-alkyl, lower-alkylthio-lower-alkyl or furyl, $R^2$ is lower-alkyl, phenyl-lower-alkyl or cyclohexyl-lower-alkyl, each of $R^3$ and $R^6$ independently is hydrogen or fluorine, each of $R^4$ and $R^5$ independently is hydrogen or lower-alkoxy or together are methylenedioxy, ethylenedioxy or ethylenoxy and n is an integer from 1 to 3, and pharmaceutically acceptable acid addition salts thereof.

These compounds are novel and are distinguished by valuable pharmacodynamic properties.

Objects of the present invention are compounds of formula I and pharmaceutically acceptable acid addition salts thereof and for use as therapeutically active substances, a process for the manufacture of these compounds, medicaments containing these compounds, and the manufacture of such medicaments as well as the use of compounds of formula I and of pharmaceutically acceptable acid addition salts thereof in the control or prevention of illnesses or in the improvement of health, especially in the control or prevention of cerebral insufficiency or in the improvement of cognitive functions, the use of compounds of formula I and of pharmaceutically acceptable acid addition salts thereof for reducing the multiple-resistance towards cytostatics in the treatment of tumors or of chloroquine resistance in the treatment of malaria and the use of compounds of formula I and of pharmaceutically acceptable acid addition salts thereof for the manufacture of medicaments for the control or prevention of cerebral insufficiency or for the improvement of cognitive functions.

DETAILED DESCRIPTION OF THE PREFERRED EMBODIMENTS

The present invention relates to tetrahydronaphthalene derivatives, and in particular, is concerned with tetrahydronaphthalene derivatives having the formula

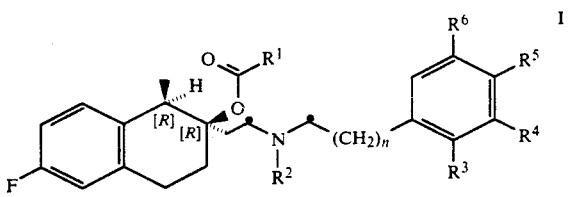

where $R^1$ is lower-alkyl, lower-alkoxy-lower-alkyl, lower-alkylthio-lower-alkyl or furyl, $R^2$ is lower-alkyl, phenyl-lower-alkyl or cyclohexyl-lower-alkyl, each of $R^3$ and $R^6$ independently is hydrogen or fluorine, each of $R^4$ and $R^5$ independently is hydrogen or lower-alkoxy or together are methylenedioxy, ethylenedioxy or ethylenoxy and n is an integer from 1 to 3, and pharmaceutically acceptable acid addition salts thereof.

These compounds are novel and are distinguished by valuable pharmacodynamic properties.

Objects of the present invention are compounds of formula I and pharmaceutically acceptable acid addition salts thereof and for use as therapeutically active substances, a process for the manufacture of these compounds, medicaments containing these compounds, and the manufacture of such medicaments as well as the use of compounds of formula I and of pharmaceutically acceptable acid addition salts thereof in the control or prevention of illnesses or in the improvement of health, especially in the control or prevention of cerebral insufficiency or in the improvement of cognitive functions, the use of compounds of formula I and of pharmaceutically acceptable acid addition salts thereof for reducing the multiple-resistance towards cytostatics in the treatment of tumors or of chloroquine resistance in the treatment of malaria and the use of compounds of formula I and of pharmaceutically acceptable acid addition salts thereof for the manufacture of medicaments for the control or prevention of cerebral insufficiency or for the improvement of cognitive functions.

The [1S,2S]-compounds corresponding to formula I, i.e. those which differ from the compounds in accordance with the invention only by the relative configuration in the 1- and 2-position, are known, for example, from U.S. Pat. No. 4,680,310. These possess a pronounced calcium-antagonist activity and are suitable for the treatment of angina pectoris, ischaemia, arrhythmias and high blood pressure.

The term "lower-alkyl" used in the present disclosure, alone or in combination, represents straight-chain and branched, saturated hydrocarbon residues with 1-4 carbon atoms, i.e. methyl, ethyl, n-propyl, isopropyl, n-butyl, isobutyl, sec.-butyl and tert.-butyl. The term "lower-alkoxy" used in the present disclosure, alone or in combination, represents lower-alkyl ether groups where "lower-alkyl" is defined above. The term "leaving group" represents conventional leaving groups such as halogen, preferably chlorine or bromine, arylsulphonyloxy such as, for example, tosyloxy, bromobenzenesulphonyloxy, benzenesulphonyloxy or mesitylenesulphonyloxy or alkylsulphonyloxy such as, for example, mesyloxy or trifluoromethylsulphonyloxy.

Those compounds of formula I where $R^1$ is lower-alkoxy-lower-alkyl or furyl, particularly methoxymethyl or 2-furyl, are preferred. n is preferably 1. Further, those compounds of formula I where $R^2$ is lower-alkyl, particularly methyl, are preferred. The compounds of formula I where each of $R^3$ and $R^6$ is hydrogen and each of R⁴ and R⁵ is independently hydrogen or lower-alkoxy, preferably methoxy, or R⁴ and R⁵ together are methylenedioxy are also preferred.

From the above it follows that those compounds of formula I where R¹ is methoxymethyl or 2-furyl, R² is methyl, each of R³ and R⁶ is hydrogen, each of R⁴ and R⁵ is independently hydrogen or methoxy or R⁴ and R⁵ together is methylenedioxy and n is 1 are especially preferred.

Quite especially preferred compounds of formula I include:

[1R,2R]-(−)-6-Fluoro-1,2,3,4-tetrahydro-1-isopropyl-2-[2-[[3,4-(methylenedioxy)phenethyl]methylamino]ethyl]-2-naphthyl methoxyacetate,

[1R,2R]-(−)-2-[2-[(3,4-dimethoxyphenethyl)methylamino]ethyl]-6-fluoro-1,2,3,4-tetrahydro-1-isopropyl-2-naphthylmethoxyacetate,

[1R,2R]-(−)-6-fluoro-1,2,3,4-tetrahydro-2-[2-[(p-methoxyphenethyl)methylamino]ethyl]-1-isopropyl-2-naphthyl methoxyactate,

[1R,2R]-(−)-6-fluoro-1,2,3,4-tetrahydro-1-isopropyl-2-[2-[[3,4-(ethylenedioxy)phenethyl]methylamino]ethyl-2-naphthyl methoxyacetate, 1R,2R]-(−)-2-[2-[[3-(3,4-dimethoxyphenyl)propyl]methylamino]ethyl]-6-fluoro-1,2,3,4-tetrahydro-1-isopropyl-2-naphthyl methoxyacetate and

[1R,2R]-(−)-2-[2-[[4-(3,4-dimethoxyphenyl)butyl]methylamino]ethyl]-6-fluoro-1,2,3,4-tetrahydro-1-isopropyl-2-naphthyl methoxyacetate.

The compounds of formula I as well as pharmaceutically acceptable acid addition salts thereof can be manufactured by reacting a compound having the formula

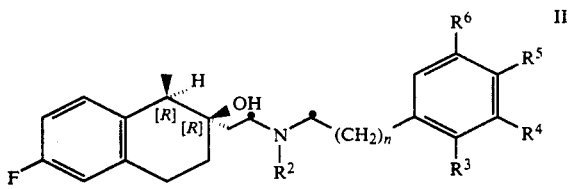

where R², R³, R⁴, R⁵, R⁶ and n are defined above, with an acylating agent yielding a lower-alkylcarbonyl, lower-alkoxy-lower-alkylcarbonyl, lower-alkylthio-lower-alkylcarbonyl or furylcarbonyl group and, if desired, converting a compound obtained into a pharmaceutically acceptable acid addition salt.

The acylation of a compound of formula II is effected according to methods well known to those of ordinary skill in the art. Suitable acylating agents are activated acid derivatives such as acid halides and acid anhydrides or mixed acid anhydrides. The reaction is carried out in an organic solvent or solvent mixture which is inert under the reaction conditions at a temperature between about 0° C. and the reflux temperature of the reaction mixture. Preferred solvents include aromatic hydrocarbons such as benzene, toluene or xylene, chlorinated hydrocarbons such as methylene chloride or chloroform, ethers such as diethyl ether, tetrahydrofuran or dioxane, and the like.

The compounds of formula II are novel and are also an object of the present invention. They can be prepared by reacting a compound having the formula

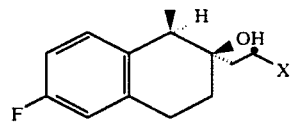

where X is a leaving group, with an amine having the formula

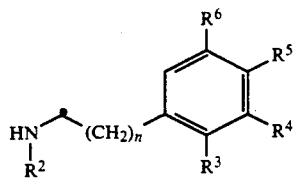

where R², R³, R⁴, R⁵, R⁶ and n are defined above.

A compound of formula III is reacted with an amine of formula IV according to methods well known to those of ordinary skill in the art. The reaction may take place in the presence or absence of an organic solvent which is inert under the reaction conditions at a temperature between about 20° and 150° C., preferably between about 80° and 120° C. Suitable solvents include dimethylformamide, dimethyl sulfoxide, alcohols such as isopropanol or tert.-butanol, ethers such as tetrahydrofuran or dioxane, aromatic hydrocarbons such as benzene, toluene or xylene, chlorinated hydrocarbons such as methylene chloride, carbon tetrachloride or chlorobenzene, and the like. The reaction of a compound of formula III and an amine of formula IV is enhanced in the presence of an acid-binding agent such as a tertiary amine, for example trimethylamine, triethylamine, ethyldiisopropylamine or 1,5-diazabicyclo[4.3.0]non-5-ene. Excess amine of formula IV can also serve as the acid-binding agent. The reaction is conveniently carried out at atmospheric pressure, although higher pressures can also be used.

The starting materials of formula III are also novel and are an object of the present invention. One procedure for their preparation is outlined in Scheme I. Specific reaction conditions are set forth in the experimental section below.

Scheme I

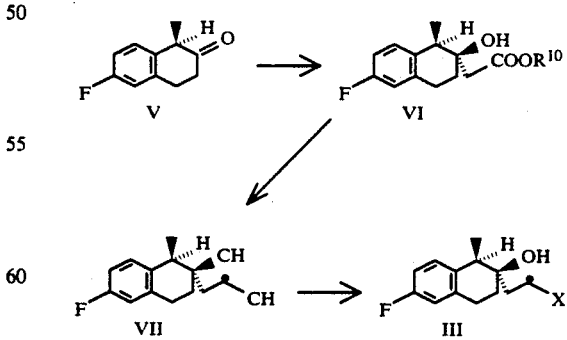

where R¹⁰ is hydrogen or lower-alkyl.

In the first step, a tetralone derivative of formula V is reacted in a manner well known to those of ordinary skill in the art with an alkyl haloacetate in the presence of zinc. The reaction with a tert.-butyl haloacetate can also be carried out in the presence of magnesium. The reaction takes place in an inert organic solvent or solvent mixture such as an ether, for example diethyl ether or tetrahydrofuran, or an aromatic hydrocarbon, for example benzene or toluene, or mixtures thereof at a temperature between about 0° C. and the reflux temperature of the solvent or solvent mixture. In situ decomposition of the addition product which is formed as an intermediate yields an ester of formula VI which can be hydrolyzed in a manner well known to those of ordinary skill in the art to the corresponding acid of formula VI.

An ester or an acid of formula VI can b e reduced, also by methods well known to those of ordinary skill in the art, to the corresponding alcohol of formula VII. Suitable reducing agents include lithium aluminum hydride, sodium bis-(2-methoxyethoxy)aluminum hydride, lithium borohydride, diiobutylaluminum hydride, diborane, and the like. The reduction is carried out in an organic, aprotic solvent which is inert under the reaction conditions such as an ether, for example diethyl ether, tetrahydrofuran or dioxane, a hydrocarbon, for example hexane or cyclohexane, or an aromatic hydrocarbon, for example benzene or toluene, and the like at a temperature between about room temperature and 100° C., preferably between about room temperature and 50° C.

An alcohol of formula VII can be converted by reaction with an arylsulphonyl halide or alkylsulphonyl halide in a manner well known to those of ordinary skill in the art into compound III where X is an arylsulphonyl or alkylsulphonyl group. This reaction is enhanced in the presence of an acid-binding agent such as a tertiary amine, for example triethylamine, ethyldiisopropylamine or pyridine, in the presence or absence of an organic solvent which is inert under the reaction conditions at a temperature between about 0° C. and 80° C. Preferred solvents include ethers such as diethyl ether, tetrahydrofuran or dioxane, aromatic hydrocarbons such as benzene or toluene, chlorinated hydrocarbons such as methylene chloride or chloroform, and the like, mixtures thereof or excess acid-binding agent. A compound of formula III where X is halogen is obtained by reacting a compound of formula III where X is arylsulphonyl or alkylsulphonyl with a sodium halide in acetone or a pyridine hydrohalide at a temperature between about 0° and 100° C.

The compounds of formulae VI and VII are novel and are also objects of the present invention, while the tetralone derivatives of formula V are either known or can be obtained in analogy to the preparation of the known compounds.

The amines of formula IV which are also used as starting materials are either well known to those of ordinary skill in the art or can be obtained in analogy to the preparation of the known compounds.

The compounds of formula I contain two asymmetric centers and are present in the absolute [R,R]-configuration indicated by formula I.

As discussed above, the tetrahydronaphthalene derivatives of formula I and their pharmaceutically acceptable acid addition salts are novel compounds having extremely valuable pharmacodynamic properties. In animal experiments described below it has been shown that these compounds are capable of counteracting cerebral insufficiency produced experimentally.

The test apparatus is a "Skinner box", whose use and construction are well known to those of ordinary skill in the art, having an electrifiable grid floor (30×40 cm) and a grey plastic platform (15×15×0.8 cm) in the front right corner. Untrained male rats (100-120 g) are placed individually on the platform. As soon as the rats climb down onto the grid floor, they receive an electric foot-shock (0.8 mA). The normal reaction of untrained rats is to jump back onto the platform. Since, however, the rats still attempt to climb down again on to the platform, the foot-shock procedure must be repeated three to five times for each animal. After three to five repetitions per animal, the rats have learned a so-called "passive avoidance response"—the rats no longer attempt to descend onto the grid floor, knowing that they will receive an electric foot-shock when they do so.

Immediately thereafter three test groups, each comprising 30 animals, were set up. The first group received an injection (i.p.) of 0.3 mg/kg of scopolamine as well as distilled water (2 ml/kg p.o.). The second group received an injection (i.p.) of 0.3 mg/kg of scopolamine and an oral dosage of the test substance. The third group received only distilled water (p.o.).

Two hours after receiving their respective injection, each rat was placed on the platform in the "Skinner box". This test is used to determine the effectiveness of a subject preparation on the short-term memory of the animals. The assessment criterion of the test is whether the animal remains or does not remain on the platform for 60 seconds (the results being "yes" or "no" for each animal). The Chi-Square test was used to determine the statistical significance of the difference between the results obtained in the first and in the second group.

Seventy to seventy-five percent of the animals in the third group remember 2-4 hours after learning the "passive avoidance response" that they should remain on the platform. In the second group, 85 to 92% of the animals established during 3-4 hours a retrograde effect on the short-term memory, forgetting that they must remain on the platform. A substance which is capable of counteracting cerebral insufficiency can reverse the blocking of the short-term memory caused by the injection (i.p.) of 0.3 mg/kg of scopolamine. A dosage of a preparation is denoted as active against scopolamine when the number of positive results ("yes") is significantly different from those of control animals treated with scopolamine (0.3 mg/kg i.p.) and only distilled water (p.o.).

Compounds of formula I and dosages which exhibit significant activity in the test described above are listed in the Table below.

TABLE

| $R^1$ | $R^2$ | $R^3$ | $R^4$ | $R^5$ | $R^6$ | n | Significant active dosage mg/kg p.o. |
|---|---|---|---|---|---|---|---|
| $CH_3OCH_2$ | $CH_3$ | H | —O—$CH_2$—O— | | H | 1 | 0.001 |
| | | | | | | | 0.003 |
| | | | | | | | 0.01 |
| | | | | | | | 0.03 |
| | | | | | | | 0.1 |
| | | | | | | | 0.3 |
| | | | | | | | 1 |
| $CH_3OCH_2$ | $CH_3$ | H | $OCH_3$ | $OCH_3$ | H | 1 | 0.1 |
| | | | | | | | 0.3 |
| | | | | | | | 1 |
| | | | | | | | 3 |
| $CH_3OCH_2$ | $CH_3$ | H | H | $OCH_3$ | H | 1 | 0.001 |
| | | | | | | | 0.003 |
| | | | | | | | 0.1 |

TABLE-continued

| R[1] | R[2] | R[3] | R[4] | R[5] | R[6] | n | Significant active dosage mg/kg p.o. |
|---|---|---|---|---|---|---|---|
| | | | | | | | 0.3 |
| | | | | | | | 1 |
| | | | | | | | 3 |
| | | | | | | | 10 |
| | | | | | | | 30 |
| $CH_3OCH_2$ | $CH_3$ | H | —O—$CH_2CH_2$—O— | | H | 1 | 0.01 |
| | | | | | | | 0.03 |
| | | | | | | | 0.1 |
| | | | | | | | 0.3 |
| $CH_3OCH_2$ | $CH_3$ | H | $OCH_3$ | $OCH_3$ | H | 2 | 0.3 |
| | | | | | | | 1 |
| $CH_3OCH_2$ | $CH_3$ | H | $OCH_3$ | $OCH_3$ | H | 3 | 0.1 |
| | | | | | | | 0.3 |

The compounds of formula I and their pharmaceutically acceptable acid addition salts can be used as medicaments, e.g., in the form of pharmaceutical preparations. The pharmaceutical preparations can be administered orally, e.g., in the form of tablets, coated tablets, dragees, hard and soft gelatine capsules, solutions, emulsions or suspensions. The administration can, however, also be effected rectally, e.g., in the form of suppositories, or parenterally, e.g., in the form of injection solutions.

As discussed above, medicaments containing a compound of formula I or a pharmaceutically acceptable acid addition salt thereof are an object of the present invention, as is a process for the manufacture of such medicaments. The process comprises bringing one or more compounds of formula I and/or pharmaceutically usable acid addition salts thereof and, if desired, one or more other therapeutically active substances into a galenical administration form together with one or more therapeutically inert, inorganic or organic excipients.

For the manufacture of tablets, coated tablets, dragees and hard gelatine capsules, there can be used as excipients lactose, maize starch or derivatives thereof, talc, stearic acid or its salts, and the like.

Suitable excipients for soft gelatine capsules include vegetable oils, waxes, fats, semi-solid and liquid polyols, and the like.

Suitable excipients for the manufacture of solutions and syrups include water, polyols, sucrose, invert sugar, glucose, and the like.

Suitable excipients for injection solutions include water, alcohols, polyols, glycerol, vegetable oils and the like.

Suitable excipients for suppositories include natural or hardened oils, waxes, fats, semi-liquid or liquid polyols and the like.

The pharmaceutical preparations additionally can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain other therapeutically valuable substances.

In accordance with the invention, the compounds of formula I and pharmaceutically acceptable acid addition salts thereof can be used in mammals to reduce the multiple-resistance towards cytostatics and chloroquine resistance in the treatment of tumors and, respectively, malaria and especially in the control or prevention of cerebral insufficiency or in the improvement of cognitive functions (such as memory capacity, learning capability, interest in the surroundings and self-care), for example in geriatry, in the case of intoxications such as alcoholism and in the case of cerebro-vascular disorders. Further fields of use include vestibular disorders (such as Meniere's disease) and development disorders (such as dyslexia). The dosage can vary within wide limits and will, of course, be fitted to the individual requirements in each particular case. In the case of oral administration, a daily dosage from about 25 to about 150 mg should be appropriate, although a greater dosage can be administered where indicated.

Finally, the use of the compounds of formula I and of pharmaceutically acceptable acid addition salts thereof for the manufacture of medicaments for the control or prevention of cerebral insufficiency or for the improvement of cognitive functions is also an object of the invention.

The following Examples are intended to illustrate the present invention, but are not intended to be limiting in any manner. All temperatures are given in degrees Celsius.

Unless otherwise indicated, the Examples were carried out as written. Unless otherwise stated, ratios relating to solvent mixtures are expressed in volume.

EXAMPLE 1

A solution of 87.4 g (0.221 mol) of [1R,2R]-(-)-6-fluoro-1,2,3,4-tetrahydro-1-isopropyl-2-[2-[[3,4-(methylenedioxy)phenethyl]methylamino]ethyl]-2-naphthalenol, 750 ml of abs. chloroform and 35.7 ml (0.21 mol) of ethyldiisopropylamine was treated dropwise while stirring at $-5°$ within 1 hour with 45.6 g (38.6 ml, 0.42 mol) of methoxyacetyl chloride and thereafter stirred for 16 hours without additional cooling. The solution was treated with ice-water, washed with 350 ml of 1N sodium hydroxide solution, dried and evaporated under reduced pressure. The residual oil (115.6 g) was dissolved in 50 ml of methanol and treated with a methanolic hydrochloric acid solution to pH 2. Ether was added to this solution until it became slightly turbid. After standing in a refrigerator for 64 hours, the white crystals were filtered off under suction and recrystallized from methanol and ether. The yield was 84.6 g (77%) of [1R,2R]-(-)-6-fluoro-1,2,3,4-tetrahydro-1-isopropyl-2-[2-[[3,4-(methylenedioxy)phenethyl]methylamino]ethyl]-2-naphthyl methoxyacetate hydrochloride, m.p. 203°–204°; $[\alpha]_D^{20} = -36.3°$ (c=1, methanol).

The [1R,2R]-(-)-6-fluoro-1,2,3,4-tetrahydro-1-isopropyl-2-[2-[[3,4-(methylenedioxy)phenethyl]methylamino]ethyl]-2-naphthalenol used as the starting material was prepared as follows:

A solution of 63.0 g (0.52 mol) of [R]-(+)-1-phenylethylamine in 800 ml of acetonitrile was added with stirring to a solution of 204.1 g (1.04 mol) of rac. 2-(p-fluorophenyl)-3-methylbutyric acid in 1200 ml of acetonitrile. After 1 hour the crystalline precipitate was filtered off, washed with 300 ml of acetonitrile and dried overnight under reduced pressure at 50°. After repeated recrystallization from ethanol, the corresponding salt was obtained as colorless crystals, m.p. 209°–210°. The salt was suspended in ether and treated with 3N hydrochloric acid to pH 1. The ethereal solution was washed with water, dried and evaporated under reduced pressure, yielding [R]-(-)-2-(p-fluorophenyl)-3-methylbutyric acid, m.p. 56°–57°; $[\alpha]_D^{20} = -48.4°$ (c=1, methanol).

A solution of 32.3 g (0.165 mol) of [R]-(—)-2-(p-fluorophenyl)-3-methylbutyric acid in 250 ml of abs. methylene chloride was treated with 27.3 ml of oxalyl chloride. After stirring at room temperature for 4 hours and evaporation of the solvent under reduced pressure, [R]-(—)-2-(p-fluorophenyl)-3-methylbutyryl chloride was obtained as an oil, b.p. 100°/65 Pa; $[\alpha]_D^{20} = -53.2°$ (c=1, chloroform).

A solution of 54.8 g (0.255 mol) of [R]-(—)-2-(p-fluorophenyl)-3-methylbutyryl chloride in 950 ml of methylene chloride was saturated at −10° with ethylene gas. The temperature was then reduced to −56° and 47.5 g (0.356 mol) of aluminum chloride in one portion were added. After 15 minutes, 10.0 g (0.075 mol) more of aluminum chloride were added thereto and the reaction mixture was left to warm slowly to −20°. Then, 500 ml of ice-water were cautiously added, and the organic phase was separated and washed with 3N hydrochloric acid and water. After drying and evaporating the solvent under reduced pressure, 59.6 g of [R]-(+)-6-fluoro-3,4-dihydro-1-isopropyl-2(1H)-naphtone were obtained as a light yellow oil; $[\alpha]_D^{20} = +189.5°$ (c=1, methanol).

7.92 g (0.32 gram atom) of magnesium were covered with 125 ml of abs. tetrahydrofuran and 5 ml of t-butyl bromoacetate were added in such a manner that the reaction starts. Thereafter, a solution of 62.2 g (0.319 mol) of t-butyl bromoacetate and 52.6 g (0.255 mol) of [R]-(+)-6-fluoro-3,4-dihydro-1-isopropyl-2(1H)-naphtone in 375 ml of abs. tetrahydrofuran were added within 30 minutes in such a manner that the reaction mixture boiled under reflux. After completion of the addition, the reaction mixture was heated to reflux for 10 minutes, thereafter cooled to 15° and finally treated with a solution of 40 g of ammonium chloride in 500 ml of water. The organic phase was separated, washed with water, dried over sodium sulphate and evaporated under reduced pressure, yielding [1R,2R]-(—)-t-butyl-6-fluoro-1,2,3,4-tetrahydro-2-hydroxy-1-isopropyl-2-naphthyl acetate as a yellow oil which was used in the next step without further purification.

A solution of 82.2 g (0.255 mol) of [1R,2R]-(—)-t-butyl-6-fluoro-1,2,3,4-tetrahydro-2-hydroxy-1-isopropyl-2-naphthyl acetate in 500 ml of abs. tetrahydrofuran was added within 30 minutes to a cooled suspension of 19.4 g (0.51 mol) of lithium aluminum hydride in 500 ml of abs. tetrahydrofuran in such a manner that the temperature did not exceed 30°. After stirring for a further 30 minutes the reaction mixture was cooled to 5° and carefully treated in succession with 30 ml of ice-water, 30 ml of 1N sodium hydroxide solution and 90 ml of ice-water. Thereafter, the mixture was stirred for a further 60 minutes and filtered, and the filtrate evaporated under reduced pressure. The oily residue was dissolved in a 20:1 mixture of chloroform and methanol and chromatographed on 900 g of silica gel, yielding [1R,2R]-(—)-2-[6-fluoro-1,2,3,4-tetrahydro-2-hydroxy-1-isopropyl-2-naphthyl]ethanol as white crystals, m.p. 78°–80°; $[\alpha]_D^{20} = -83.1°$ (c=1, methanol).

28.5 g (0.113 mol) of [1R,2R]-(—)-2-[6-fluoro-1,2,3,4-tetrahydro-2-hydroxy-1-isopropyl-2-naphthyl]ethanol were dissolved in 150 ml of pyridine and treated portionwise within 30 minutes at 0° with 31.5 g (0.165 mol) of p-toluenesulphonyl chloride. After 90 minutes the reaction solution was poured into ice-water and extracted with ether. The organic phase was washed in succession with 3N hydrochloric acid, water and a saturated sodium carbonate solution. After drying over magnesium sulphate and evaporation of the solvent under reduced pressure, the remaining oily residue was recrystallized from ether/hexane, yielding 38.8 g (85%) of [1R,2R]-(—)-2-[6-fluoro-1,2,3,4-tetrahydro-2-hydroxy-1-isopropyl-2-naphthyl]ethyl p-toluenesulphonate as white crystals, m.p. 65°–67°; $[\alpha]_D^{20} = -54.1°$ (c=1, methanol).

A solution of 12.6 g (0.031 mol) of [1R,2R]-(—)-2-[6-fluoro-1,2,3,4-tetrahydro-2-hydroxy-1-isopropyl-2-naphthyl]ethyl p-toluenesulphonate, 6.1 g (0.031 mol) of 3,4-(methylenedioxy)-N-methyl-β-phenethylamine and 5.3 ml (0.031 mol) of ethyldiisopropylamine in 50 ml of dimethyl sulfoxide was stirred under a nitrogen atmosphere for 3 hours at 80° and thereafter concentrated in a high vacuum. The residue was dissolved in methylene chloride and the solution obtained was washed with a saturated sodium carbonate solution and extracted three times with 3N hydrochloric acid. The aqueous extracts were made alkaline with a 28% sodium hydroxide solution. The oily suspension was extracted three times with methylene chloride. The organic extracts were dried and evaporated under reduced pressure. The residual oil was chromatographed on silica gel with ethyl acetate/methanol (9:1), yielding 9.3 g (73%) of [1R,2R]-(—)-6-fluoro-1,2,3,4-tetrahydro-1-isopropyl-2-[[3,4-(methylenedioxy)phenethyl]methylamino]ethyl]-2-naphthalenol as a yellowish oil; $[\alpha]_D^{20} = -22.1°$.

The following compounds were manufactured in an analogous manner to that described above:

from [1R,2R]-(—)-2-[6-fluoro-1,2,3,4-tetrahydro-2-hydroxy-1-isopropyl-2-naphthyl]ethyl p-toluenesulphonate and N-methylhomoveratrylamine the [1R,2R]-(—)-2-[2-[(3,4-dimethoxyphenethyl)methylamino]ethyl]-6-fluoro-1,2,3,4-tetrahydro-1-isopropyl-2-naphthalenol hydrochloride, m.p. 165°–166° (from ethyl acetate/ether); $[\alpha]_D^{20} = -45.1°$ (c=1, methanol);

from [1R,2R]-(—)-2-[6-fluoro-1,2,3,4-tetrahydro-2-hydroxy-1-isopropyl-2-naphthyl]ethyl p-toluenesulphonate and N-methyl-β-phenylethylamine the [1R,2R]-(—)-6-fluoro--1,2,3,4-tetrahydro-1-isopropyl-2-[2-[(phenethyl)methylamino]ethyl]-2-naphthalenol as a light yellow oil which was used directly in the next step;

from [1R,2R]-(—)-2-[6-fluoro-1,2,3,4-tetrahydro-2-hydroxy-1-isopropyl-2-naphthyl]ethyl p-toluenesulphonate and N-methyl-β-(p-methoxyphenethylamine) the [1R,2R]-(—)-6-fluoro-1,2,3,4-tetrahydro-1-isopropyl-2-[2-[(p-methoxyphenethyl)methylamino]ethyl]-2-naphthalenol as a light yellowish oil which was used directly in the next step;

from [1R,2R]-(—)-2-[6-fluoro-1,2,3,4-tetrahydro-2-hydroxy-1-isopropyl-2-naphthyl]ethyl p-toluenesulphonate and 3,4-(methylenedioxy)-N-ethyl-β-phenylethylamine the [1R,2R]-(—)-2-[2-[ethyl[3,4-(methylenedioxy)phenethyl]-amino]ethyl]-6-fluoro-1,2,3,4-tetrahydro-1-isopropyl-2-naphthalenol as a light brown oil which was used directly in the next step;

from [1R,2R]-(—)-2-[6-fluoro-1,2,3,4-tetrahydro-2-hydroxy-1-isopropyl-2-naphthyl]ethyl p-toluenesulphonate and 3,4-(methylenedioxy)-N-benzyl-β-phenethylamine the [1R,2R]-(—)-2-[2[benzyl[3,4-(methylenedioxy)phenethyl]-amino]ethyl]-6-fluoro-1,2,3,4-tetrahydro-1-isopropyl-2-naphthalenol as a light yellow oil which was used directly in the next step;

from [1R,2R]-(—)-2-[6-fluoro-1,2,3,4-tetrahydro-2-hydroxy-1-isopropyl-2-naphthyl]ethyl p-toluenesulphonate and 3,4-(ethylenedioxy)-N-methyl-β-phenethylamine the [1R,2R]-(—)-6-fluoro-1,2,3,4-tetrahydro-1-isopropyl-2-]-[[3,4-(ethylenedioxy)phenethyl]methylamino]ethyl]-2-naphthalenol as a light yellow mass which was used directly in the next step;

from [1R,2R]-(—)-2-[6-fluoro-1,2,3,4-tetrahydro-2-hydroxy-1-isopropyl-2-naphthyl]ethyl p-toluenesulphonate and N-methyl-3,4-dimethoxy-γ-phenylpropylamine the [1R,2R]-(—)-2-[2-[[3-(3,4-dimethoxyphenyl)propyl]methylamino]ethyl]-6-fluoro-1,2,3,4-tetrahydro-1-isopropyl-2 -naphthalenol as a light yellow oil which was used directly in the next step and from [1R,2R]-(—)-2-[6-fluoro-1,2,3,4-tetrahydro-2-hydroxy-1-isopropyl-2-naphthyl]ethyl p-toluenesulphonate and N-methyl-3,4-dimethoxy-β-phenylbutylamine the [1R,2R]-(—)-2-[2-[[4-(3,4-dimethoxyphenyl)butyl]methylamino]ethyl]-6-fluoro-1,2,3,4-tetrahydro-1-isopropyl-2-naphthalenol as a light yellow mass which was used directly in the next step.

EXAMPLE 2

The following compounds were manufactured in an analogous manner to that described in Example 1:

from [1R,2R]-(—)-6-fluoro-1,2,3,4-tetrahydro-1-isopropyl-2-[2-[[3,4(methylenedioxy)phenethyl]methylamino]ethyl]-2-naphthalenol and acetyl chloride, the [1R,2R]-(—)-6-fluoro-1,2,3,4-tetrahydro-1-isopropyl-2-[2-[[3,4-(methylenedioxy)phenethyl]methylamino]ethyl]-2-naphthyl acetate hydrochloride as a light yellow solid, $[\alpha]_D^{20} = -36.9°$ (c=1, methanol)];

from [1R,2R]-(—)-6-fluoro-1,2,3,4-tetrahydro-1-isopropyl-2-[2-[[3,4-(methylenedioxy)phenethyl]methylamino]ethyl]-2-naphthalenol and propionyl chloride, the [1R,2R]-(—)-6-fluoro-1,2,3,4-tetrahydro-1-isopropyl-2-[2-[[3,4-(methylenedioxy)phenethyl]methylamino]ethyl]-2-naphthyl propionate hydrochloride as a light brown mass, $[\alpha]_D^{20} = -32.9°$ (c=1, methanol);

from [1R,2R]-(—)-6-fluoro-1,2,3,4-tetrahydro-1-isopropyl-2-[2-[[3,4-(methylenedioxy)phenethyl]methylamino]ethyl]-2-naphthalenol and methylthioacetyl chloride the [1R,2R]-(—)-6-fluoro-1,2,3,4-tetrahydro-1-isopropyl-2-[2-[[3,4-(methylenedioxy)phenethyl]methylamino]ethyl]-2-naphthyl(methylthio)acetate hydrochloride as a light brown mass, $[\alpha]_D^{20} = -27.5°$ (c=1, methanol);

from [1R,2R]-(—)-6-fluoro-1,2,3,4-tetrahydro-1-isopropyl-2-[2-[[3,4-(methylenedioxy)phenethyl]methylamino]ethyl]-2-naphthalenol and 3-furoyl chloride the [1R,2R]-(—)-6-fluoro-1,2,3,4-tetrahydro-1-isopropyl-2-[2-[[3,4-methylenedioxy]phenethyl]methylamino]ethyl]-2-naphthyl-3-furancarboxylate hydrochloride as a light yellow mass, $[\alpha]_D^{20} = -39.3°$ (c=1, methanol);

from [1R,2R]-(—)-2-[2-[(3,4-dimethoxyphenethyl)methylamino]ethyl]-6-fluoro-1,2,3,4-tetrahydro-1-isopropyl-2-naphthalenol and methoxyacetyl chloride, the [1R,2R]-(—)-2-[2-[(3,4-dimethoxyphenethyl)methylamino]ethyl]-6-fluoro-1,2,3,4-tetrahydro-1-isopropyl-2-naphthyl methoxyacetate hydrochloride, m.p. 174°175°, $[\alpha]_D^{20} = =35°$ (c=1, methanol);

from [1R,2R]-(—)-2-[2-[(3,4-dimethoxyphenylethyl)methylamino]ethyl]-6-fluoro-1,2,3,4-tetrahydro-1-isopropyl-2-naphthalenol and acetyl chloride, the [1R,2R]-(—)-2-[2-[(3,4-dimethoxyphenethyl)methylamino]ethyl]-6-fluoro-1,2,3,4-tetrahydro-1-isopropyl-2-naphthyl acetate hydrochloride as a light yellow mass, $[\alpha]_D^{20} = -41°$ (c=1, methanol);

from [1R,2R]-(—)-2-[2-[(3,4-dimethoxyphenethyl)methylamino]ethyl]-6-fluoro-1,2,3,4-tetrahydro-1-isopropyl-2-naphthalenol and n-butyryl chloride, and [1R,2R]-(—)-2-[2-[(3,4-dimethoxyphenethyl)methylamino]ethyl]-6-fluoro-1,2,3,4-tetrahydro-1-isopropyl-2-naphthyl valerate hydrochloride as a light brown mass, $[\alpha]_D^{20} = -31.1°$ (c=1, methanol);

from [1R,2R]-(—)-6-fluoro-1,2,3,4-tetrahydro-1-isopropyl-2-[2-[(phenethyl)methylamino]ethyl]-2-naphthanenol and methoxyacetyl chloride, the [1R,2R]-(—)-6-fluoro-1,2,3,4-tetrahydro-1-isopropyl-2-[2-(methylphenethylamino)ethyl]-2-naphthyl methoxyacetate hydrochloride as colorless crystals, m.p. 185°-190° (from ethyl acetate), $[\alpha]_D^{20} = -37.8°$ (c=1, methanol);

from [1R,2R)-(—)-6-fluoro-1,2,3,4-tetrahydro-1-isopropyl-2-[2-[(p-methoxyphenethyl)methylamino]ethyl]-2-naphthanenol and methoxyacetyl chloride the [1R,2R]-(—)-6-fluoro-1,2,3,4-tetrahydro-2-[2-[(p-methoxyphenethyl)methylamino]ethyl]-1-isopropyl-2-naphthyl methoxyacetate hydrochloride as a light yellowish mass, $[\alpha]_D^{20} = -35.1°$ (c=1, methanol);

from [1R,2R]-(—)-2-[2-[ethyl[3,4-(methylenedioxy)phenethyl]amino]ethyl]-6-fluoro-1,2,3,4-tetrahydro-1-isopropyl-2-naphthalenol and methoxyacetyl chloride, the [1R,2R]-(—)-2-[2-[ethyl[3,4-(methylenedioxy)phenethyl]amino]ethyl]-6-fluoro-1,2,3,4-tetrahydro-1-isopropyl-2-naphthyl methoxyacetate hydrochloride as a light brown mass, $[\alpha]_D^{20} = -22.0°$ (c=1, methanol);

from [1R,2R]-(—)-2-[2-[benzyl[3,4-(methylenedioxy)phenethyl]amino]ethyl]-6-fluoro-1,2,3,4-tetrahydro-1-isopropyl-2-naphthalenol and methoxyacetyl chloride, the [1R,2R]-(—)-2-[2-[benzyl[3,4-(methylenedioxy)phenethyl]amino]ethyl]-6-fluoro-1,2,3,4-tetrahydro-1-isopropyl-2-naphthyl methoxyacetate hydrochloride as a light yellow mass, $[\alpha_D^{20} = -32.4°$ (c=1, methanol);

from [1R,2R]-(—)-6-fluoro-1,2,3,4-tetrahydro-1-isopropyl-2-[2-[methyl[3,4-(ethylenedioxy)phenethyl]amino]ethyl]-2-naphthalenol and methoxyacetyl chloride. the [1R,2R]-(—)-6-fluoro-1,2,3,4-tetrahydro-1-isopropyl-2-[2-[methyl(3,4-(ethylenedioxy)phenethyl]amino]ethyl]-2-naphthyl methoxyacetate hydrochloride as a light brown mass, $[\alpha]_D^{20} = -30.7°$ (c=1, methanol);

from [1R,2R]-(—)-2-[2-[[3-(3,4-dimethoxyphenyl)propyl]methylamino]ethyl]-6-fluoro-1,2,3,4-tetrahydro-1-isopropanol-2-naphthalenol and methoxyacetyl chloride, the [1R,2R]-(—)-2-[2-[[3-(3,4-dimethoxyphenyl)propyl]methylamino]ethyl]-6-fluoro-1,2,3,4-tetrahydro-1-isopropyl-2-naphthyl methoxyacetate hydrochloride as a light yellow foam, $[\alpha]_D^{20} = -30.5°$ (c=1, methanol) and from [1R,2R]-(—)-2-[2-[[4-(3,4-dimethoxyphenyl)butyl]methylamino]ethyl]-6-fluoro-1,2,3,4-tetrahydro-1-isopropyl-2-naphthalenol and methoxyacetyl chloride, the [1R,2R]-(—)-2-[2-[[4-(3,4-dimethoxyphenyl)butyl]methylamino]ethyl]-6-1,2,3,4-tetrahydro-1-isopropyl-2-naphthyl methoxyacetate hydrochloride as a light brown foam, $[\alpha]_D^{20} = -27.5°$ (c=1, methanol).

EXAMPLE 3

In an analogous manner to that described in Example 1, from [1R,2R]-(—)-2-[6-fluoro-1,2,3,4-tetrahydro-2-hydroxy-1-isopropyl-2-hydroxy-1-isopropyl-2-naphthyl]ethyl p-toluenesulphonate and N-methyl-(2,5-difluorohomoveratrylamine), the corresponding naphthalenol was obtained as a viscous oil which was reacted directly with methoxyacetyl chloride to give

[1R,2R]-(−)-[2-[2-(2,5-difluoro-3,4-dimethoxyphenethyl)methylamino]ethyl]-6-fluoro-1,2,3,4-tetrahydro-1-isopropyl-2-napthyl methoxyacetate hydrochloride in the form of a light brown foam, $[\alpha]_D^{20} = -31.3°$ (c=1, methanol).

EXAMPLE 4

In an analogous manner to that described in Example 1, from [1R,2R]-(-)-2-[6-fluoro-1,2,3,4-tetrahydro-2-hydroxy-1-isopropyl-2-napthyl]ethyl p-toluenesulphonate and N-methyl-(2-fluorohomoveratrylamine), the corresponding naphthalenol was obtained as a viscous oil which was reacted directly with methoxyacetyl chloride to give [1R,2R]-(-)-2-[2-[(2-fluoro-3,4-dimethoxyphenethyl)methylamino]ethyl]-6-fluoro-1,2,3,4-tetrahydro-1-isopropyl-2-naphthyl methoxyacetate hydrochloride in the form of a light brown mass, $[\alpha]_D^{20} = -31.8°$ (c=1, methanol).

EXAMPLE A

| Tablets Composition: | |
|---|---|
| (1) [1R,2R]-(−)-6-Fluoro-1,2,3,4-tetrahydro-1-isopropyl-2-[2-[[3,4-(methylenedioxy)-phenethyl]methylamino]ethyl]-2-naphthyl methoxyacetate hydrochloride | 75 mg |
| (2) Powd. lactose | 135 mg |
| (3) White maize starch | 55 mg |
| (4) Povidone K 30 | 15 mg |
| (5) White maize starch | 15 mg |
| (6) Talc | 3 mg |
| (7) Magnesium stearate | 2 mg |
| Tablet weight | 300 mg |

Manufacturing Procedure 1-3 are mixed intensively. The mixture is then moistened with an aqueous solution of 4 and kneaded, and the resulting mass is granulated dried and sieved. The granulate is mixed with 5-7 and pressed into tablets of suitable size.

EXAMPLE B

| Tablets Composition: | | |
|---|---|---|
| (1) [1R,2R]-(−)-6-Fluoro-1,2,3,4-tetrahydro-1-isopropyl-2-[2-[[3,4-(methylenedioxy)-phenethyl]methylamino]ethyl]-2-naphthyl methoxyacetate hydrochloride | 75 mg | 60 mg |
| (2) Powd. lactose | 100 mg | 100 mg |
| (3) Maize starch | 60 mg | 60 mg |
| (4) Povidone K 30 | 5 mg | 5 mg |
| (5) Maize starch | 15 mg | 15 mg |
| (6) Sodium carboxymethylstarch | 5 mg | 5 mg |
| (7) Talc | 3 mg | 3 mg |
| (8) Magnesium stearate | 2 mg | 2 mg |
| Tablet weight | 265 mg | 250 mg |

Manufacturing Procedure 1-3 are mixed intensively. The mixture is then moistened with an aqueous solution of 4 and kneaded, and the resulting mass is granulated, dried and sieved. The granulate is mixed with 5-7 and pressed into tablets of suitable size.

EXAMPLE C

| Tablets Composition: | | |
|---|---|---|
| (1) [1R,2R]-(−)-6-Fluoro-1,2,3,4-tetrahydro-1-isopropyl-2-[2-[[3,4-(methylenedioxy)-phenethyl]methylamino]ethyl]-2-naphthyl methoxyacetate hydrochloride | 75 mg | 90 mg |
| (2) Powd. lactose | 46 mg | 46 mg |
| (3) Microcrystalline cellulose | 60 mg | 60 mg |
| (4) Povidone K 30 | 10 mg | 10 mg |
| (5) Sodium carboxymethylstarch | 4 mg | 4 mg |
| (6) Talc | 3 mg | 3 mg |
| (7) Magnesium stearate | 2 mg | 2 mg |
| Tablet weight | 200 mg | 215 mg |

Manufacturing Procedure 1-3 are mixed intensively. The mixture is then moistened with an aqueous solution of 4 and kneaded, and the resulting mass granulated, dried and sieved. The granulate is mixed with 5-7 and pressed into tablets of suitable size.

EXAMPLE D

| Capsules Composition: | |
|---|---|
| (1) [1R,2R]-(−)-6-Fluoro-1,2,3,4-tetrahydro-1-isopropyl-2-[2-[[3,4-(methylenedioxy)-phenethyl]methylamino]ethyl]-2-naphthyl methoxyacetate hydrochloride | 75 mg |
| (2) Cryst. lactose | 100 mg |
| (3) White maize starch | 20 mg |
| (4) Talc | 9 mg |
| (5) Magnesium stearate | 1 mg |
| Capsule fill weight | 205 mg |

Manufacturing Procedure

The active substance is mixed intensively with the lactose. This mixture is then admixed with the maize starch, the talc and the magnesium stearate and the mixture is filled into capsules of suitable size.

EXAMPLE E

| Capsules Composition: | |
|---|---|
| (1) [1R,2R]-(−)-6-Fluoro-1,2,3,4-tetrahydro-1-isopropyl-2-[2-[[3,4-(methylenedioxy)-phenethyl]methylamino]ethyl]-2-naphthyl methoxyacetate hydrochloride | 75 mg |
| (2) Microcrystalline cellulose | 100 mg |
| (3) Sodium carboxymethylstarch | 5 mg |
| (4) Talc | 9 mg |
| (5) Magnesium stearate | 1 mg |
| Capsule fill weight | 190 mg |

Manufacturing Procedure

The active substance is mixed intensively with the cellulose. This mixture is then admixed with the sodium carboxymethylstarch, the talc and the magnesium stearate and the mixture is filled into capsules of suitable size.

EXAMPLE F

| Injection solution | |
|---|---|
| [1R,2R]-(−)-6-Fluoro-1,2,3,4-tetrahydro-1-isopropyl-2-[2-[[3,4-(methylenedioxy)-phenethyl]methylamino]ethyl]-2-naphthyl methoxyacetate hydrochloride | 8 mg |
| Pure cryst. sodium chloride | 8.5 mg |
| Water for injection add | 1 ml |

EXAMPLE G

When the procedures described in Examples A through F are followed, tablets, capsules and injection preparations can be manufactured from the following likewise preferred compounds and their pharmaceutically acceptable salts:

[1R,2R]-(-)-2-[2-[(3,4-Dimethoxyphenethyl)methylamino]-ethyl]-6-fluoro-1,2,3,4-tetrahydro-1-isopropyl-2-naphthyl methoxyacetate hydrochloride,

[1R,2R]-(-)-6-fluoro-1,2,3,4-tetrahydro-2-[2-[(p-methoxyphenethyl) methylamino]ethyl]-1-isopropyl-2-naphthyl methoxyacetate hydrochloride,

[1R,2R]-(-)-6-fluoro-1,2,3,4-tetrahydro-1-isopropyl-2-[2-[[3,4-(ethylenedioxy)phenethyl]methylamino]ethyl]-2-naphthyl methoxyacetate hydrochloride,

[1R,2R]-(-)-2-[2-[[3-(3,4-dimethoxyphenyl)propyl]methylamino]ethyl]-6-fluoro-1,2,3,4-tetrahydro-1-isopropyl-2-naphthyl methoxyacetate hydrochloride and

[1R,2R]-(-)-2-[2-[[4-(3,4-dimethoxyphenyl)butyl]methylamino]ethyl]-6-fluoro-1,2,3,4-tetrahydro-1-isopropyl-2-naphthyl methoxyacetate hydrochloride.

We claim:

1. A method of treating mammals to improve short-term memory comprising administering a compound of the formula

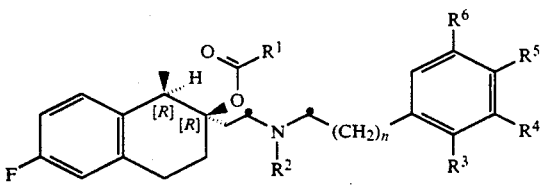

wherein $R^1$ is lower-alkyl, lower-alkoxy-lower-alkyl, lower-alkylthio-lower-alkyl or furyl, $R^2$ is lower-alkyl, phenyl-lower-alkyl or cyclohexyl-lower-alkyl, each of $R^3$ and $R^6$ independently is hydrogen or fluorine, each of $R^4$ and $R^5$ independently is hydrogen or lower-alkoxy or together are methylenedioxy, ethylenedioxy or ethylenoxy and n is an integer from 1 to 3 or pharmaceutically acceptable acid addition salts thereof in an amount which is effective for improving short-term memory.

2. The method of claim 1, wherein $R^1$ is lower-alkoxy-lower-alkyl or furyl.

3. The method of claim 2, wherein $R^1$ is methoxymethyl or 2-furyl.

4. The method of claim 1, wherein n is 1.

5. The method of claim 1, wherein $R^2$ is lower-alkyl.

6. The method of claim 5, wherein $R^2$ is methyl.

7. The method of claim 1, wherein each of $R^3$ and $R^6$ is hydrogen.

8. The method of claim 1, wherein each of $R^4$ and $R^5$ independently is hydrogen or lower-alkoxy.

9. The method of claim 8, wherein each of $R^4$ and $R^5$ independently is hydrogen or methoxy.

10. The method of claim 1, wherein $R^4$ and $R^5$ together are methylenedioxy.

11. The method of claim 1, wherein $R^1$ is methoxymethyl or 2-furyl, $R^2$ is methyl, each of $R^3$ and $R^6$ is hydrogen, each of $R^4$ and $R^5$ independently is hydrogen, methoxy or together methylenedioxy and n is 1.

12. The method of claim 1, wherein the compound is [1R,2R]-(-)-2-[2-[(3,4-Dimethoxyphenethyl) methylamino]ethyl]-6-fluoro-1,2,3,4-tetrahydro-1-isopropyl-2-naphthyl methoxyacetate.

13. The method of claim 1, wherein the compound is [1R,2R]-(-)-6-Fluoro-1,2,3,4-tetrahydro-2-[2-[(p-methoxyphenethyl)methylamino]ethyl]-1-isopropyl-2-naphthyl methoxyacetate.

14. The method of claim 1, wherein the compound is [1R,2R]-(-)-6-Fluoro-1,2,3,4-tetrahydro-1-isopropyl-2-2-[[3,4-(ethylenedioxy) phenethyl]methtylamino]ethyl]-2-naphthyl methoxyacetate.

15. The method of claim 1, wherein the compound is [1R,2R]-(-)-2-[2-[[3-(3,4-Dimethoxyphenyl)propyl]methylamino]ethyl]-6-fluoro-1,2,3,4-tetrahydro-1-isopropyl-2-naphtyl methoxyacetate.

16. The method of claim 1, wherein the compound is [1R,2R]-(-)-2-[2-[[4-(3,4-Dimethoxyphenyl)butyl]methylamino]ethtyl]]-6-fluoro-1,2,3,4-tetrahydro-1-isopropyl-2-naphtyl methoxyacetate.

17. The method of claim 1, wherein compound I is administered in a daily dosage amount from about 25 to about 150 mg.

18. The method of claim 17, wherein compound I is [1R,2R]-(-)-6-fluoro-1,2,3,4-tetrahydro-1-isopropyl-2-2-[[3,4,-(methylenedioxy)phenethyl]methylaminoethyl]-2-naphtyl methoxyacetate.

* * * * *